United States Patent

Timmerman et al.

[11] Patent Number: 6,107,308
[45] Date of Patent: Aug. 22, 2000

[54] PIPERIDINE DERIVATIVES

[75] Inventors: Hendrik Timmerman, Voorschoten, Netherlands; Mingqiang Zang, Scotland, United Kingdom; Kazuhiro Onogi; Yoshio Takahashi, both of Iruma, Japan; Masahiro Tamura; Tsutomu Tohma, both of Higashimurayama, Japan; Yasushi Wada, Tachikawa, Japan; Jiro Matsumoto, Sayama, Japan; Toru Kanke, Higashimurayama, Japan

[73] Assignee: Kowa Co., Ltd., Nagoya, Japan

[21] Appl. No.: 09/158,775

[22] Filed: Sep. 23, 1998

[30] Foreign Application Priority Data

Sep. 25, 1997 [JP] Japan .................................. 9-259848
Sep. 26, 1997 [JP] Japan .................................. 9-261599

[51] Int. Cl.$^7$ .................................................. A61K 31/47
[52] U.S. Cl. ............................ 514/314; 514/312; 514/307; 514/309; 514/224.2; 514/213; 540/523; 540/594; 544/51; 546/158; 546/165; 546/176
[58] Field of Search .................................... 514/314, 312, 514/307, 309, 224.2, 213; 540/523, 594; 544/51; 546/158, 165, 176

[56] References Cited

U.S. PATENT DOCUMENTS 5,756,518   5/1998   Timmerman et al. .................. 514/314

FOREIGN PATENT DOCUMENTS 0 613 897     9/1994   European Pat. Off. .
WO 91/19475  12/1991   WIPO .
PCT/JP
98/03054      7/1998   WIPO .

Primary Examiner—D. Margaret Seaman
Attorney, Agent, or Firm—Oblon, Spivak, McClelland, Maier & Neustadt, P.C.

[57] ABSTRACT

The present invention is directed to a piperidine derivative represented by the following formula (1) or a salt thereof:

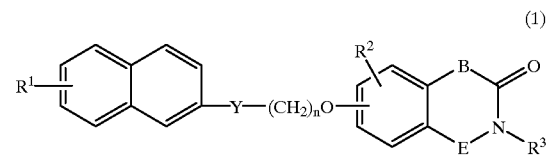

(1)

wherein $R^1$, $R^2$, and $R^3$ individually represent hydrogen atoms, etc., Y represents

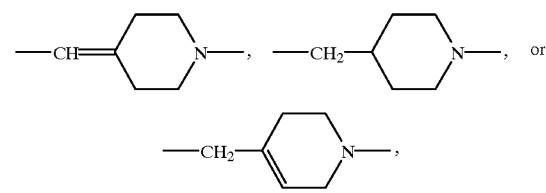

B represents a single bond, an alkylene group, —S—CH$_2$—, or —CH═CH—, E represents a single bond or a trimethylene group, Z represents an oxygen atom, etc., and n represents a number between 2 and 5 inclusive; and to a medicine containing the compound. The medicine according to the present invention is endowed with excellent antihistaminic activity and antileukotriene activity, and exhibits reduced side effects such as drowsiness.

4 Claims, No Drawings

PIPERIDINE DERIVATIVES

BACKGROUND OF THE INVENTION

1. Field of the Invention

The present invention relates to a piperidine derivative and salts thereof, which have excellent antihistaminic activity and antileukotriene activity and are useful as a medicine for broad range of allergic diseases.

2. Background Art

Histamine, which contracts bronchial smooth muscle and promotes capillary permeability when coupled to an $H_1$ receptor prevailing on the cell membrane, is a significant mediator in allergic diseases. More specifically, histamine is considered to trigger the aggravation of various symptoms of asthma due to its bronchial contractire action, and also to increase the leakage of blood components into intercellular space due to its increasing effect on vascular permeability, to thereby participate in the onset mechanism of allergic rhinitis and the formation of edema in conjunctivitis, etc. In the treatment of allergic diseases as mentioned above, antihistaminic agents have been used. However, conventional antihistaminic agents involve the fear of causing adverse side effects to central nervous system, such as drowsiness, when the agent is coupled to an $H_1$ receptor in the brain. In recent years, bronchial asthma is considered a chronic airway inflammation until the infiltration of eosinocytes participate. In this connection, attention has been drawn to a late asthma response which manifests airway constriction unique to asthma as a result of infiltration of inflammation cells into bronchial mucosa and hypersecretion from the mucosa.

In the meantime, leukotrienes (LTs) participate in most inflammatory diseases including asthma, psoriasis, rheumatism, and inflammatory colitis, and thus play an important role in inflammation caused by cytotoxic reactions.

Thus, on the basis of the finding that leukotrienes are predominant mediators in allergic reactions and inflammations, there have been discovered a number of substances that suppress the action or the synthesis of leukotrienes in an attempt to relieve these pathological conditions (S. T. Holgate et al.: J. Allergy Clin. Immunol. 98, 1–13 (1996)).

Leukotrienes are arachidonic acid metabolites synthesized by 5-lipoxygenase (5-LO) and are divided into two groups. One group refers to $LTB_4$ and exhibits strong chemotaxis towards leukocytes. The other group collectively encompasses cysteine leukotrienes (CysLTs), including $LTC_4$, $LTD_4$, and $LTE_4$; these substances have long been called "slow-reacting substances of anaphylaxis (SRS-A)." In human tissues, CysLTs exert actions when they are coupled with their receptors. It has been found that a selective $LTD_4$ receptor inhibitor suppresses the contraction action of both $LTC_4$ and $LTD_4$ in human lung tissue, suggesting that the binding site of an $LTD_4$ receptor f or $LTD_4$ also serves as a binding site for $LTC_4$ (Buckner C. K. et al.: Ann. NY Acad. Sci. 1988, 524; 181–186, Aharony D. et al.: New Trends in Lipid Mediators Research, Basel: Karger 1989; 67–71). $LTE_4$ is also considered to exert its action by the mediation of the same receptor available for $LTD_4$. But since its activity is low, $LTE_4$ is considered to be a partially active substance.

Briefly, in allergic diseases such as asthma, pathological profiles of immediate asthma response—i.e., bronchoconstriction and formation of edema in which histamine and similar mediators participate—and those of late asthma response—i.e., airway constriction as a result of cellular infiltration, mucous secretion, hyperplasia of membrane, etc. in which leukotrienes participate—are deemed to play a significant role in the manifestation of pathological conditions. Similarly, the pathological profile of allergic rhinitis also comes to be elucidated as a two-phase reaction including an immediate asthma response phase manifesting ptarmus and hypersecretion of pituita and a late asthma response phase manifesting nasal congestion due to swollen nasal membrane; wherein histamine participates in the former and leukotriene participates in the latter.

Accordingly, it is considered that a compound which exhibits antagonism against both a histamine $H_1$ receptor and an $LTD_4$ receptor and which minimally migrates into the brain can serve as a medicine having reduced side effects and is effective for the prevention and treatment of a variety of symptoms from the immediate asthma response phase to the delayed response phase of a broad range of allergic diseases, in particular asthma and rhinitis.

However, until realization of the present invention, a compound exhibiting sufficient antagonism against both the histamine $H_1$ receptor—which relates to the immediate asthma response phase—and the $LTD_4$ receptor—which relates to the late asthma response phase—had not yet been found. Moreover, many $LTD_4$ antagonists which are now being developed have at least one acid group in the molecule and are hydrophilic compounds having high polarity, and inevitably they are not sufficiently absorbed by oral route, leading to an increase in dose of these types of drugs and causing side effects.

SUMMARY OF THE INVENTION

In view of the foregoing, the present inventors have conducted extensive studies in search for a compound which has both antihistaminic activity and anti-leukotriene activity and which does not have the aforementioned drawbacks, and have found that the compound represented by the following formula (1) satisfactorily meets the present purposes, to thereby complete the present invention.

Accordingly, an object of the present invention is to provide a novel compound which has antihistaminic activity and anti-leukotriene activity, which minimally migrates into the brain, and which has no acid group in the molecule.

In one aspect of the present invention, there is provided a piperidine derivative or a salt thereof represented by the following formula (1):

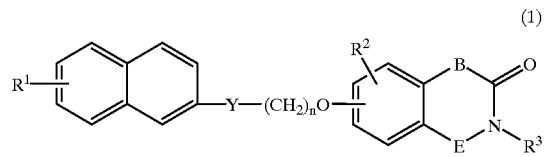

wherein $R^1$ represents a hydrogen atom or a halogen atom, $R^2$ represents a hydrogen atom or a lower alkyl group, Y represents

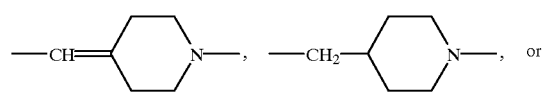

-continued

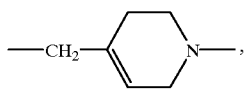

B represents a single bond,

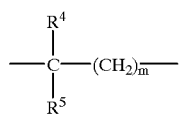

(wherein each of $R^4$ and $R^5$, which are identical to or different from each other, represents a hydrogen atom or a lower alkyl group, and m represents a number between 0 and 2 inclusive), —S—CH$_2$—, or —CH=CH—, n represents a number between 2 and 5 inclusive, Z is an oxygen atom and $R^3$ is a hydrogen atom, or $R^3$ and Z may join with the adjacent nitrogen atom to form a tetrazolyl group, and E represents a single bond or a trimethylene group, provided that when B is a single bond, E is a trimethylene group, and when B is a group other than a single bond, E is a single bond.

In another aspect of the present invention, there is provided a medicine comprising as an active ingredient a piperidine derivative represented by the above-described formula (1) or a salt thereof.

In still another aspect of the present invention, there is provided a pharmaceutical composition comprising a piperidine derivative represented by the above-described formula (1) or a salt thereof, and a pharmacologically acceptable carrier.

In yet another aspect of the present invention, there is provided use, as a medicine, of a piperidine derivative represented by the above-described formula (1) or a salt thereof.

In yet another aspect of the present invention, there is provided a method for the treatment of allergic diseases, which method comprises administering to a patient in need thereof an effective amount of a piperidine derivative represented by the above-described formula (1) or a salt thereof.

In yet another object of the present invention, there is provided a method for the treatment of a disease selected from the group consisting of asthma, allergic rhinitis, allergic conjunctivitis, atopic dermatitis, urticaria, psoriasis, rheumatism, inflammatory colitis, cerebral ischemia, and cerebral apoplexy, which method comprises administering to a patient in need thereof an effective amount of a piperidine derivative represented by the above-described formula (1) or a salt thereof.

BEST MODE FOR CARRYING OUT THE INVENTION

In the piperidine derivative of formula (1), examples of the halogen atom represented by $R^1$ include a fluorine atom, a chlorine atom, a bromine atom, and an iodine atom. Preferably, $R^1$ is a hydrogen atom. The lower alkyl groups represented by $R^2$, $R^4$, or $R^5$ include C1–C6 linear or branched alkyl groups. Specific examples thereof include a methyl group, an ethyl group, a n-propyl group, an i-propyl group, a n-butyl group, an i-butyl group, a sec-butyl group, a t-butyl group, a pentyl group, and a hexyl group. Of these groups, a methyl group is preferred.

No particular limitation is imposed on the salts of the compounds of the present invention represented by formula (1), so long as they are pharmacologically acceptable. Examples of such salts include acid adducts of mineral acids, such as hydrochlorides, hydrobromides, hydroiodides, sulfates and phosphates; acid adducts of organic acids, such as benzoates, methanesulfonates, ethanesulfonates, benzenesulfonates, p-toluenesulfonates, oxalates, maleates, fumarates, tartarates and citrates.

The compound of formula (1) of the present invention (hereinafter may be referred to as compound (1)) may take the form of a solvate such as a hydrate, and the present invention encompasses such a solvate.

Also, the compound (1) may take the form of a ketoenol tautomer, and the present invention encompasses such a tautomer.

The compound (1) of the present invention may be prepared by, for example, according to the methods described below.

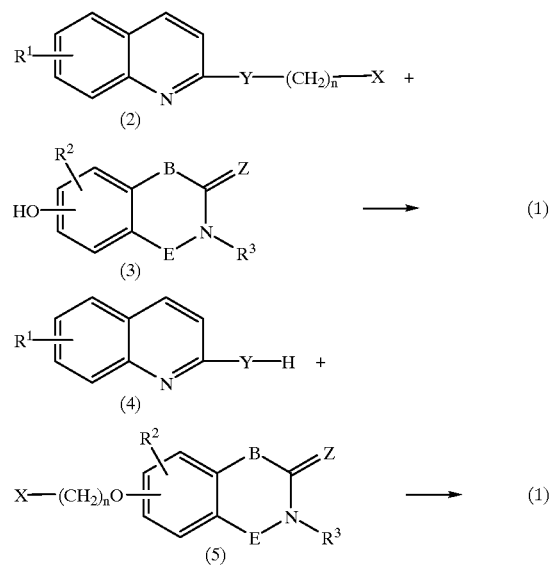

wherein $R^1$ through $R^3$, Y, Z, B, E, and n have the same meanings as described above, and X represents a halogen atom.

Briefly, the compound (1) of the present invention may be prepared by causing a reaction between a haloalkylated piperidine derivative (2) and a phenolic compound (3), or between a piperidien derivative (4) and a haloalkylated phenolic compound (5), in an inert gas stream, without use of any solvent or in the presence of an aprotic solvent such as acetone, 2-butanone, dimethylformamide (DMF), dimethylsulfoxide (DMSO), or hexamethylphosphoramide (HMPA) with the application of heat (preferably 100–200° C.) for 1–24 hours.

The piperidine derivative of formula (4) may be prepared through the following synthesis route.

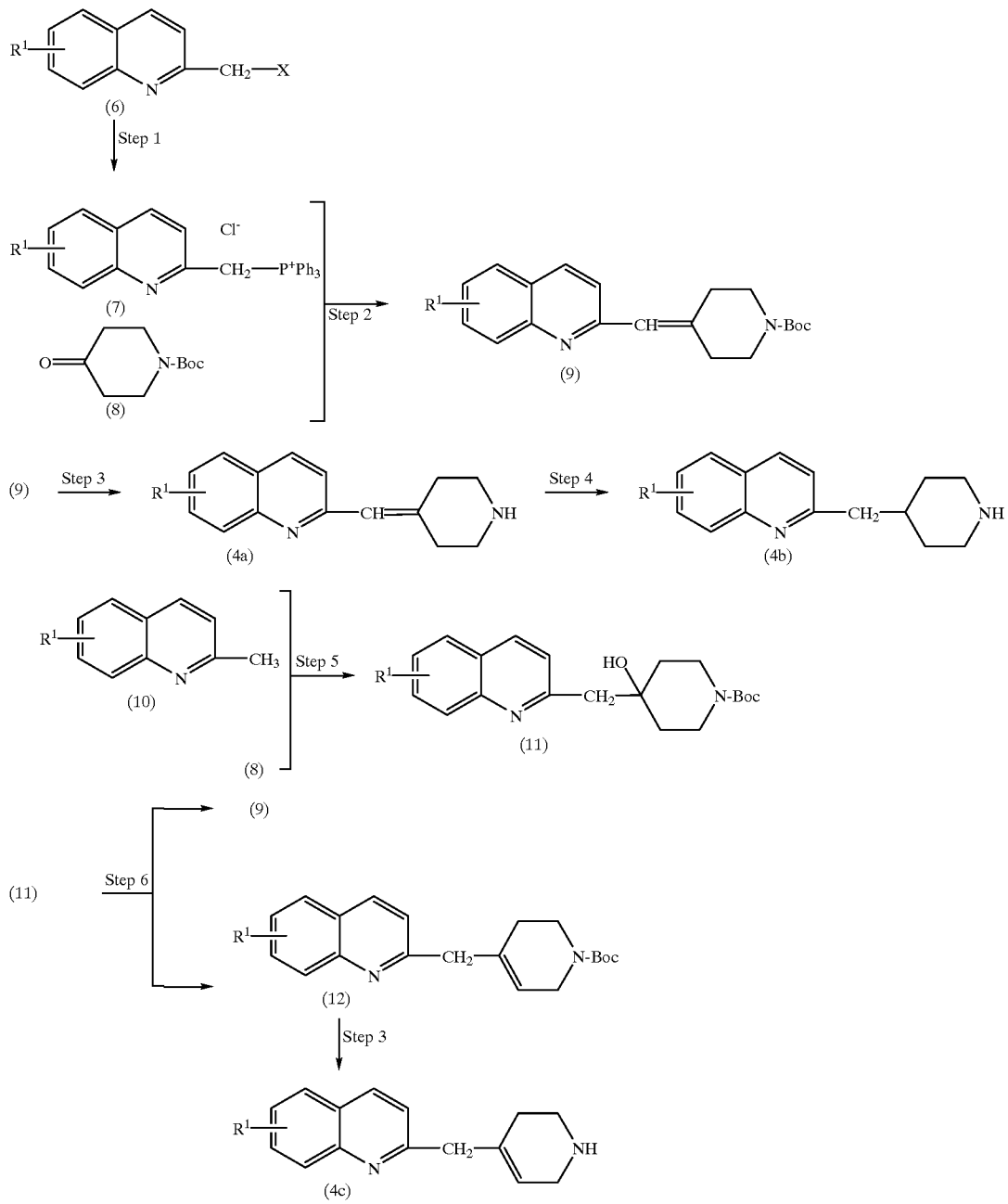

wherein $R^1$ and X have the same meanings as described above, Ph stands for phenyl, and Boc stands for t-butoxycarbonyl.

Briefly, a compound (6) and triphenylphosphine are caused to react with each other in the presence of a nonpolar solvent such as toluene, benzene, etc. at a temperature between 0° C. and a reflux temperature, preferably at a reflux temperature, for one night to several days, to thereby obtain a phosphonium salt (7). The phosphonium salt (7) is transformed into a compound (9) by the following process. First, butyl lithium is added to the phosphonium salt (7) in a polar solvent such as tetrahydrofuran, dioxane, or a similar solvent at a temperature between −78° C. and room temperature, preferably at 0° C. Subsequently, a compound (8) is added for reaction for one night to several days at a temperature between 0° C. and a reflux temperature, preferably at room temperature, to thereby obtain a compound (9). When the compound (9) is treated with an acid, for example, a hydrochloride solution of ethyl acetate or trifluoroacetic acid at a temperature between 0° C. and a reflux temperature, preferably at room temperature, a compound (4a) is obtained. The thus-obtained compound (4a) is converted into a compound (4b) through hydrogenation performed at a temperature between 0° C. and a reflux temperature, preferably at room temperature, in the presence of a metal catalyst such as palladium in a polar solvent such as water, methanol, or ethanol.

A compound (4c) having an unsaturated bond in the piperidine ring may be prepared as follows. First, butyl lithium is added to a compound (10) in a polar solvent such as tetrahydrofuran or dioxane at a temperature between −78° C. and room temperature, preferably at 0° C. Subsequently, a compound (8) is added thereto for causing a reaction for one night to several days, to thereby obtain a compound (11). The compound (11) is allowed to react with a sulfonyl chloride such as methane sulfonyl chloride or toluene sulfonyl chloride for several hours to several days in a polar solvent such as tetrahydrofuran or dioxane, at a temperature between 0° C. and a reflux temperature, preferably at room temperature, and then with a base such as 1,8-diazabicyclo [5.4.0]undec-7-ene (DBU) at a temperature between 0° C. and a reflux temperature, preferably at room temperature, in a nonpolar solvent such as toluene or benzene for one night to several days, to thereby obtain a compound (12) having an unsaturated bond in the piperidine ring, and the aforementioned compound (9). When the compound (12) is subjected to acid treatment by use of a hydrochloride solution of ethyl acetate or trifluoroacetic acid at a temperature between 0° C. and a reflux temperature, preferably at room temperature, the compound (12) can be transformed to the compound (4c).

The compounds (2) and (5) may be respectively prepared by reacting the compound (4) or (3) with a dihalogenated compound of a linear alkane in an aprotic solvent such as acetone, 2-butanone, DMF, DMSO, or HMPA at a temperature between 0° C. and a reflux temperature, preferably at reflux temperature, for 1–24 hours.

Suitable known compounds may serve as the compounds (3), (6), (8), and (10). Alternatively, these compounds may be prepared by known methods described, for example, in Musser, John H. et al.; J. Med. Chem. 33(1), 240–245, 1990, Iemura, Ryuichi et al.; J. Heterocyclic. Chem. 24(1), 31–37, 1987, Mathes, W., Schuly, H: Angew. Chem. 75, 235–240, 1963, Lambourne, H. et al.; J. Chem. Soc. 119, 1294–1300, 1921.

After completion of the above-described sequence of reactions, a suitable treatment of the obtained compound according to a customary method provides a target compound of the present invention, which may further be purified by a customary purification means such as recrystallization, column chromatography, etc., as desired. If necessary, the compound may be converted into any one of the aforementioned salts through a method known per se.

The thus-obtained compounds (1) and their salts of the present invention exhibit excellent anti-leukotriene activity and excellent antihistaminic activity, as demonstrated by the below-described examples. Moreover, they transfer to the centrum in lesser amounts as compared with terfenadine. Thus, the present compounds are useful as a medicine for a broad range of allergic diseases such as asthma, allergic rhinitis, and allergic dermatitis such as atopic dermatitis, allergic conjunctivitis, urticaria, psoriasis, rheumatism, and inflammatory colitis; as well as cerebral ischemia and cerebral apoplexy.

The medicine of the present invention comprises as an active ingredient the above-described compound (1), a salt thereof, or a hydrate of the compound (1) or the salt. Examples of the manner of administration of the present medicine include oral administrations by way of tablets, capsules, granules, powders, and syrups and non-oral administrations such as intravenous injections, intramuscular injections, suppositories, inhalations, percutaneous absorptions, eye drops, and nasal drops. In order to prepare pharmaceutical preparations of a variety of forms, the aforementioned active ingredient may be used alone or in combination with a pharmaceutical vehicle, such as, for example, an excipient, a binder, a bulking agent, a disintegrant, a surfactant, a lubricant, a dispersing agent, a buffering agent, a preservative, a flavoring agent, a perfume, a coating agent, carrier, a diluent, etc.

The dosage of the medicine of the present invention varies in accordance with the age, body weight, symptom, manner of administration, frequency of the administration, etc. In general, in the case of adults, it is preferred that the compound of the present invention is administered in an amount of 1–1,000 mg per day at a time or as divided in several times, orally or non-orally.

EXAMPLES

The present invention will next be described by way of examples, which should not be construed as limiting the invention thereto.

Production Example 1

Synthesis of 1-tert-butoxycarbonyl-4-ketopiperidine:

4-Ketopiperidine hydrochloride (48.3 g) and di-tert-butyl carbonate (93.2 g) were dissolved in a dioxane-water equivolume mixture (1000 ml), and triethylamine (119 ml) was added to the resultant mixture. The mixture was stirred at room temperature for five hours and concentrated under reduced pressure. Water and ethyl acetate were added to the residue. After separation of the organic phase, the organic phase was washed with a saturated solution of potassium hydrogensulfate and water, dried over sodium sulfate anhydrate, and concentrated under reduced pressure, to thereby obtain the title compound as a colorless solid.

Yield: 59.4 g (81%)

NMR (CDCl$_3$): δ1.49(9H,s), 2.44(4H, t, J=6.2 Hz), 3.71 (4H, t, J=6.2 Hz)

mp 74~75° C.

Production Example 2

Synthesis of 2-quinolylmethyltriphenylphosphonium chloride:

2-Chloromethylquinoline hydrochloride (10.7 g) was dissolved in water (50 ml), and the solution was neutralized with potassium carbonate. The resultant mixture was extracted with ethyl acetate. The organic phase was washed with saturated brine, dried over sodium sulfate anhydrate, and concentrated under reduced pressure. The resultant oily matter was dissolved in toluene (50 ml), and triphenylphosphine (13.1 g) was added thereto. The mixture was heat-refluxed overnight, and then allowed to cool. Crystals that precipitated were collected and washed with toluene, to thereby obtain the title compound as colorless powder. This powder was used for subsequent reaction without further purification.

Yield: 18.44 g (83%)

NMR (DMSO): δ5.71(2H, d, J=5.1 Hz), 7.53–7.61(3H, m), 7.66–7.75(7H, m), 7.80–7.96 (10H, m), 8.34(1H, d, J=8.3 Hz)

m.p. 230° C. or more

Production Example 3

Synthesis of 1-tert-butoxycarbonyl-4-(2-quinolylmethylene)piperidine:

Under argon, 2-quinolylmethyltriphenylphosphonium chloride (8.72 g) was dissolved in anhydrous THF (60 ml), and a 1.6N solution (15 ml) of butyllithium was added dropwise over 20 minutes under cooling on ice. The mixture was then stirred for 10 minutes at room temperature. To the mixture, an anhydrous THF (24 ml) solution of 1-tert-butoxycarbonyl-4-ketopiperidine (4.29 g) was added dropwise over 15 minutes under cooling on ice. The mixture was stirred for 30 minutes under cooling on ice and further stirred overnight at room temperature. Water (200 ml) was added to the reaction mixture, then the resultant mixture was extracted with ether. The organic phase was back-extracted with 1N hydrochloric acid, and the aqueous phase was neutralized with a saturated solution of sodium hydrogencarbonate. The resultant mixture was extracted with ethyl acetate. The organic phase was washed with saturated brine, dried over sodium sulfate anhydrate, and concentrated under reduced pressure, to thereby obtain the title compound as a solid. This solid was used for subsequent reaction without further purification.

Yield: 5.19 g (80%)

NMR (CDCl$_3$): δ1.48(9H, s), 2.43(2H, t, J=5.7 Hz), 2.94(2H, t, J=5.7 Hz), 3.48(2H, t, J=5.7 Hz), 3.55(2H, t, J=5.7 Hz), 6.58(1H, s), 7.29(1H, d, J=8.5 Hz), 7.45–7.52(1H, m), 7.65–7.11(1H, m), 7.77(1H, dd, J=8.0, 1.3 Hz), 8.03(1H, dd, J=8.0, 0.7 Hz), 8.09(1H, d, J=8.3 Hz), mp 72~73° C.

Production Example 4

Synthesis of 4-(2-quinolylmethylene)piperidine:

1-tert-Butoxycarbonyl-4-(2-quinolylmethylene) piperidine (17.6 g) was dissolved in dichloromethane (60 ml), and TFA (60 ml) was added to the solution under cooling on ice. The mixture was stirred for 2.5 hours at room temperature and concentrated under reduced pressure. A saturated solution of sodium hydrogencarbonate was added to the residue to neutralize, and the mixture was then extracted with chloroform. The organic phase was dried over sodium sulfate anhydrate and concentrated under reduced pressure. The title compound was recovered from an ether-hexane solvent as white powder. This powder was also used for subsequent reaction without further purification.

Yield: 9.62 g (89%)

NMR (CDCl$_3$): δ2.65(2H, t, J=5.4 Hz), 3.13–3.33(6H, m), 6.57(1H, s), 7.27(1H, d, J=8.5 Hz), 7.47–7.54(1H, m), 7.65–7.73(1H, m), 7.77(1H, dd, J=8.0, 1.0 Hz), 8.02(1H, dd, J=8.0, 0.7 Hz), 8.10(1H, d, J=8.3 Hz), mp 131~132° C.

Production Example 5

Synthesis of 4-(2-quinolylmethyl)piperidine:

4-(2-Quinolylmethylene)piperidine (9.62 g) was dissolved in ethanol (500 ml), and 10% palladium-carbon (1.9 g) was added to the solution. The mixture was stirred under a hydrogen stream at room temperature for 90 minutes. After removal of the catalyst by filtration, the filtrate was concentrated under reduced pressure, to thereby obtain the title compound as a colorless solid.

Yield: 9.02 g (92%)

NMR (CDCl$_3$): δ1.70(2H, dd, J=13.5, 4.0 Hz), 1.89(2H, br d, J=13.5 Hz), 2.19–2.36(1H, m), 2.86(2H, dt, J=13.5, 3.0 Hz), 2.95(2H, d, J=7.3 Hz), 3.39(2H, br d, J=13.5 Hz), 7.23(1H, d, J=8.3 Hz), 7.48–7.54(1H, m), 7.67–7.74(1H, m), 7.80(1H, dd, J=8.0, 1.0 Hz), 8.03(1H, d, J=8.5 Hz), 8.09(1H, d, J=8.3 Hz)

mp 166~167° C.

Production Example 6

Synthesis of 1-tert-butoxycarbonyl-4-hydroxy-4-(2-quinolylmethyl)piperidine:

2-Methylquinoline hydrochloride (7.14 g) was dissolved in water (50 ml), and the solution was neutralized with a saturated solution of potassium carbonate. The resultant solution was extracted with ethyl acetate, and the organic phase was washed with saturated brine, dried over sodium sulfate anhydrate, and concentrated under reduced pressure. The resultant residue was dissolved in anhydrous THF (120 ml), and a 1.6N solution (30 ml) of butyllithium was added dropwise to solution over 20 minutes under cooling on ice. The mixture was then stirred for 10 minutes at room temperature. To the mixture, an anhydrous THF (50 ml) solution of 1-tert-butoxycarbonyl-4-ketopiperidine (9.97 g) was added dropwise over 15 minutes under cooling on ice. The mixture was stirred for 30 minutes under cooling on ice and further stirred for 1.5 hours at room temperature. Water (400 ml) was added to the reaction mixture, then the resultant mixture was extracted with ether. The organic phase was back-extracted with 1N hydrochloric acid, and the aqueous phase was neutralized with a saturated solution of sodium hydrogencarbonate. The resultant mixture was extracted with ethyl acetate. The organic phase was washed with saturated brine, dried over sodium sulfate anhydrate, and concentrated under reduced pressure. The residue was purified through silica gel column chromatography (developer: ether-hexane (1:1)), to thereby obtain the title compound as white powder.

Yield: 5.95 g (34%)

NMR (CDCl$_3$): δ1.45(9H, s), 1.50–1.68(4H, m), 3.07(2H, s), 3.26(2H, br t, J=10.0 Hz), 3.82(2H, br d, J=10.0 Hz), 7.23(1H, d, J=8.5 Hz), 7.49–7.56(1H, m), 7.68–7.75(1H, m), 7.81(1H, d, J=8.3 Hz), 8.00(1H, d, J=8.5 Hz), 8.12(1H, d, J=8.3 Hz)

mp 119~121° C.

Production Example 7

Synthesis of 1-tert-butoxycarbonyl-4-(2-quinolylmethyl)-1,2,5,6-tetrahydropyridine:

1-tert-Butoxycarbonyl-4-hydroxy-4-(2-quinolylmethyl) piperidine (5.95 g) was dissolved in anhydrous THF (50 ml), and methane sulfonylchloride (2.99 g) and triethylamine (7.3 ml) were added to the solution. The mixture was stirred at room temperature for two hours and concentrated under reduced pressure. Water and ethyl acetate were added to the mixture to thereby separate an organic phase, which was further washed with saturated brine, dried over sodium sulfate anhydrate, and concentrated under reduced pressure. The residue was dissolved in toluene (50 ml), and DBU (5.30 g) was added to the solution. The mixture was stirred at 60° C. for three hours and concentrated under reduced pressure. Water and ethyl acetate were added to the mixture to thereby separate an organic phase, which was further washed with saturated brine, dried over sodium sulfate anhydrate, and concentrated under reduced pressure. The resultant residue was subjected to silica gel column chromatography (developer: hexane-ethyl acetate (1:1)). The title compound was obtained through crystallization from hexane.

Yield: 2.59 g (45%)

NMR (CDCl$_3$): δ1.44(9H,s), 2.10(2H, br s), 3.43(2H, t, J=5.7 Hz), 3.70(2H, s), 3.90(2H, br s), 5.45(1H, br s), 7.31(1H, d, J=8.5 Hz), 7.47–7.54(1H, m), 7.66–7.73(1H, m), 7.79(1H, dd, J=8.0, 1.2 Hz), 8.06(1H, dd, J=7.8, 0.5 Hz), 8.09(1H, d, J=8.0 Hz)

Production Example 8

Synthesis of 4-(2-quinolylmethyl)-1,2,5,6-tetrahydropyridine:

1-tert-Butoxycarbonyl-4-(2-quinolylmethyl)-1,2,5,6-tetrahydropyridine (1.98 g) was dissolved in dichloromethane (5 ml), and TFA (5 ml) was added to the solution under cooling on ice. The mixture was stirred for 2.5 hours at room temperature and concentrated under reduced pressure. A saturated solution of sodium hydrogencarbonate was added to the residue to neutralize, the mixture was then extracted with chloroform. The organic phase was dried over sodium sulfate anhydrate and concentrated under reduced pressure. The title compound was recovered from an ether-hexane solvent as white powder. This powder was also used for subsequent reaction without further purification.

Yield: 1.07 g (78%)

NMR (CDCl$_3$): δ1.99–2.12(3H, m), 2.94(2H, t, J=5.7 Hz), 3.36(2H, s), 3.66(2H, s), 5.54(1H, s), 7.34(1H, d, J=8.55 Hz), 7.47–7.54(1H, m), 7.65–7.73(1H, m), 7.79(1H, d, J=8.1 Hz), 8.06(1H, d, J=8.3 Hz), 8.07(1H, d, J=8.3 Hz)

Example 1

Synthesis of 4-[3-[4-(2-quinolylmethylene)piperidino]propoxy]-3,3,7-trimethyl-2,3-dihydro-1H-indol-2-one:

4-(3-Chloropropoxy)-3,3,7-trimethyl-2,3-dihydro-1H-indol-2-one (268 mg) and 4-(2-quinolylmethylene)piperidine (224 mg) were dissolved in DMF (10 ml), and potassium carbonate (145 mg) and potassium iodide (173 mg) were added to the solution. The mixture was stirred at 100° C. for 90 minutes under argon and concentrated under reduced pressure. Chloroform was added to the residue. The mixture was washed with water, dried over magnesium sulfate anhydrate, and concentrated under reduced pressure. The residue was subjected to silica gel column chromatography (developer: chloroform-methanol (20:1)), to thereby obtain the title compound.

Yield: 298 mg (65%)

NMR (CDCl$_3$): δ1.46(6H, s), 1.97–2.09(2H, m), 2.18(3H, s), 2.48–2.68(8H, m), 3.01(2H, t, J=5.4 Hz), 4.06(2H, t, J=6.0 Hz), 6.49(1H, d, J=8.0 Hz), 6.52(1H, s), 6.94(1H, d, J=8.0 Hz), 7.31(1H, d, J=8.0 Hz), 7.44–7.51(1H, m), 7.56 (1H, br S), 7.64–7.71(1H, m), 7.76(1H, dd, J=8.0, 1.0 Hz), 8.03(1H, d, J=8.5 Hz), 8.7(1H, d, J=8.7 Hz)

mp 186~190° C.

Examples 2 to 14

In a manner similar to that in Example 1, the compounds shown in Table 1 were obtained.

TABLE 1

| Ex. | Compound | m.p. |
|---|---|---|
| 2 | 7-[3-[4-(2-Quinolylmethylene)piperidino]propoxy]-3,4-dihydro-2H-1,4-benzothiazin-3-one | 177 ~ 179° C. |
| 3 | 8-Methyl-5-[3-[4-(2-quinolylmethylene)piperidino]propoxy]-1,2,3,4-tetrahydroquinolin-2-one | 147 ~ 149° C. |
| 4 | 6-[2-[4-(2-Quinolylmethylene)piperidino]ethoxy]-1,2,3,4-tetrahydroquinolin-2-one | 190 ~ 193° C. (decomposed) |
| 5 | 6-[3-[4-(2-Quinolylmethylene)piperidino]propoxy]-1,2,3,4-tetrahydroquinolin-2-one | 160 ~ 163° C. (decomposed) |
| 6 | 6-[4-[4-(2-Quinolylmethylene)piperidino]butoxy]-1,2,3,4-tetrahydroquinolin-2-one | 168 ~ 170° C. (decomposed) |
| 7 | 6-[5-[4-(2-Quinolylmethylene)piperidino]pentoxy]-1,2,3,4-tetrahydroquinolin-2-one | 105 ~ 108° C. (decomposed) |
| 8 | 8-[3-[4-(2-Quinolylmethylene)piperidino]propoxy]-1,2,3,4-tetrahydroquinolin-2-one oxalate | (decomposed) |
| 9 | 7-[3-[4-(2-Quinolylmethylene)piperidino]propoxy]-1,2,3,4-tetrahydroquinolin-2-one oxalate | 163 ~ 164° C. (decomposed) |
| 10 | 8-Methyl-5-[2-[4-(2-quinolylmethylene)-piperidino]ethoxy]carbostyryl | 192 ~ 194° C. (decomposed) |
| 11 | 8-Methyl-5-[3-[4-(2-quinolylmethylene)-piperidino]propoxy]carbostyryl | 170 ~ 173° C. (decomposed) |
| 12 | 7-[3-[4-(2-Quinolylmethylene)piperidino]propoxy]-2,3,4,5-tetrahydro-1H-benz[b]azepin-2-one oxalate | 180 ~ 183° C. (decomposed) |
| 13 | 7-[3-[4-(2-Quinolylmethylene)piperidino]propoxy]-2,3,4,5-tetrahydro-1H-benz[c]azepin-1-one oxalate | 118 ~ 120° C. (decomposed) |
| 14 | 8-[3-[4-(2-Quinolylmethylene)piperidino]propoxy]-5,6-dihydro-4H-tetrazolo[1,5-a]benz[b]azepine oxalate | 164 ~ 166° C. (decomposed) |

Example 15

Synthesis of 4-[3-[4-(2-quinolylmethyl)piperidino]-propoxy]-3,3,7-trimethyl-2,3-dihydro-1H-indol-2-one:

In a manner similar to that described in Example 1, 4-(3-chloropropoxy)-3,3,7-trimethyl-2,3-dihydro-1H-indol-2-one (268 mg) and 4-(2-quinolylmethyl)piperidine (226 mg) were processed, to thereby obtain the title compound as white powder.

Yield: 544 mg (59%)

NMR (CDCl$_3$): δ1.45(6H, m), 1.34–1.63(2H, m), 1.63–1.76(2H, m), 1.84–2.05(5H, m), 2.19(3H, s), 2.51(2H, t, J=6.8 Hz), 2.86–2.97(4H, m), 4.01(2H, t, J=5.9 Hz), 6.47(1H, d, J=8.3 Hz), 6.92(1H, d, J=8.3 Hz), 7.26(1H, d, J=8.3 Hz), 7.49(1H, t, J=6.8 Hz), 7.64–7.74(1H, m, Ar-H), 7.78(1H, d, J=8.3 Hz), 8.02–8.12(3H, m)

mp 150~151° C.

Examples 16 to 28

In a manner similar to that in Example 15, the compounds shown in Table 2 were obtained.

TABLE 2

| Ex. | Compound | m.p. |
|---|---|---|
| 16 | 7-[3-[4-(2-Quinolylmethyl)piperidino]propoxy]-3,4-dihydro-2H-1,4-benzothiazin-3-one | 124 ~ 125° C. |
| 17 | 8-Methyl-5-[2-[4-(2-quinolylmethyl)piperidino]ethoxy]-1,2,3,4-tetrahydroquinolin-2-one | 125 ~ 126° C. |
| 18 | 8-Methyl-5-[3-[4-(2-quinolylmethyl)piperidino]propoxy]-1,2,3,4-tetrahydroquinolin-2-one | 145 ~ 147° C. |
| 19 | 6-[2-[4-(2-Quinolylmethyl)piperidino]ethoxy]-1,2,3,4-tetrahydroquinolin-2-one | 165 ~ 166° C. |
| 20 | 6-[3-[4-(2-Quinolylmethyl)piperidino]propoxy]-1,2,3,4-tetrahydroquinolin-2-one | 136 ~ 137° C. |
| 21 | 6-[4-[4-(2-Quinolylmethyl)piperidino]butoxy]-1,2,3,4-tetrahydroquinolin-2-one | 165 ~ 166° C. |
| 22 | 6-[5-[4-(2-Quinolylmethyl)piperidino]pentoxy]-1,2,3,4-tetrahydroquinolin-2-one | 124 ~ 125° C. |
| 23 | 7-[3-[4-(2-Quinolylmethyl)piperidino]propoxy]-1,2,3,4-tetrahydroquinolin-2-one | 120 ~ 121° C. |
| 24 | 8-[3-[4-(2-Quinolylmethyl)piperidino propoxy]-1,2,3,4-tetrahydroquinolin-2-one oxalate | 152 ~ 154° C. |
| 25 | 8-Methyl-5-[2-[4-(2-quinolylmethyl)-piperidino]ethoxy]carbostyryl | 151 ~ 154° C. |
| 26 | 8-Methyl-5-[3-[4-(2-quinolylmethyl)-piperidino]propoxy]carbostyryl | 161 ~ 163° C. (decomposed) |
| 27 | 7-[3-[4-(2-Quinolylmethyl)piperidino]propoxy]-2,3,4,5-tetrahydro-1H-benz[b]azepin-2-one oxalate | 108 ~ 111° C. |
| 28 | 7-[3-[4-(2-Quinolylmethyl)piperidino]propoxy]-2,3,4,5-tetrahydro-1H-benz[c]azepin-1-one | 118 ~ 120° C. |

Example 29

Synthesis of a 7-[3-[4-(2-quinolylmethyl)-1,2,5,6-tetrahydropyridyl]propoxy]-1,2,3,4-tetrahydroquinolin-2-one oxalate:

In a manner similar to that described in Example 1, 7-(3-chloropropoxy)-1,2,3,4-tetrahydroquinolin-2-one (240 mg) and 4-(2-quinolylmethyl)-1,2,5,6-tetrahydropyridine (226 mg) were processed, to thereby obtain the title compound as white powder.

Yield: 284 mg (66%)

NMR (DMSO-$d_6$): δ2.03–2.16(2H, m), 2.29–2.38(2H, m), 2.41(2H, dd, J=8.0, 6.2 Hz), 2.79(2H, t, J=8.0 Hz), 3.14–3.32(4H, m), 3.64–3.76(4H, m), 3.96(2H, t, J=5.5 Hz), 5.55(1H, br s), 6.42(1H, d, J=2.5 Hz), 6.48(1H, dd, J=8.3, 2.5 Hz), 7.04(1H, d, J=8.3 Hz), 7.45(1H, d, J=8.3 Hz), 7.53–7.61(1H, m), 7.69–7.77(1H, m), 7.95(2H, d, J=8.5 Hz), 8.31(1H, d, J=8.5 Hz), 10.0(1H, s)

m.p. 117° C. (decomposed)

Test Example 1

Antihistaminic action and antileukotriene action (in vitro test):

A guinea pig was subjected to ileectomy, and the ileum was cut to have a length of about 2 cm. Each piece of ileum was suspended in a Tyrode's buffer placed in a 20-ml organ bath. Isotonic contraction in response to histamine or leukotriene $D_4$ was recorded by use of a recording apparatus. The Tyrode's buffer was aerated with a gas mixture (95% $O_2$–5% $CO_2$) while the temperature of the buffer was maintained at 30° C. Antihstaminic activity was tested by adding $10^{-8}$ to $10^{-4}$ M histamine to the organ bath and obtaining a dose-response curve. After washing with a buffer several times, a test compound was added to the organ bath. Thirty minutes later, another dose-response curve of histamine was obtained. For the test of antileukotriene activity, effects exerted by addition of a $10^{-5}$ M test compound on the contraction included with $10^{-8}$ M $LTD_4$ was investigated. In Table 3, antihistminic action is indicated by $pA_2$ or $pD'_2$, whereas antileukotriene action is indicated by inhibition exerted by a test compound at a concentration of $10^{-5}$ M, or by $IC_{50}$.

TABLE 3

| Example | Anti-histaminic action | | $LTD_4$ action(%) ($10^{-5}$ M) |
|---|---|---|---|
| 2 | $pD'_2$ | 8.22 | 21 |
| 3 | $pA_2$ | 9.85 | 77 |
| 8 | $pA_2$ | 9.65 | 30 |
| 9 | $pA_2$ | 8.53 | 15 |
| 10 | $pA_2$ | 10.08 | 61 |
| 11 | $pA_2$ | 9.66 | 39 |
| 12 | $pA_2$ | 9.75 | 12 |
| 13 | $pA_2$ | 9.76 | 39 |
| 14 | $pA_2$ | 10.28 | 40 |
| 15 | $pA_2$ | 9.49 | 19 |
| 16 | $pD'_2$ | 8.01 | 15 |
| 17 | $pA_2$ | 9.78 | 23 |
| 25 | $pA_2$ | 9.33 | 88 |
|   |   |   | $3.4 \times 10^{-6}$ M($IC_{50}$) |
| 26 | $pA_2$ | 9.79 | 29 |

Example 2

$H_1$ receptor binding inhibitory test:

50 mM phosphate buffer (pH 7.5, 1 ml) containing 0.3 nM [$^3$H] mepyramine (activity: 22 Ci/mmol), guinea pig cerebral membrane protein, and a test compound was incubated at 37° C. for 30 minutes. Reaction was stopped by addition of ice-cold phosphate buffer, and immediately thereafter, the reaction mixture was filtered by use of a Wattman CF/C filter. The filter was washed twice, each time with 20 ml ice-cold buffer. Radioactivity of the residue was measured by use of a liquid scintillation counter. From the value as obtained when a test compound was not added and values as obtained when the test compound was added at different concentrations, there was determined a dose-response curve representing suppression action of the test compound, from which a 50% inhibitory concentration ($IC_{50}$) was obtained. Based on the $IC_{50}$ value and by use of the Cheng-Prusoff equation, a dissociation constant ($K_D$) was calculated (Table 4). In a saturation test, $10^{-4}$ M R(–)-dimethindene was used for the measurement of the amount of non-specific binding.

From the saturation test, it was found that a single type of receptor was involved, and the saturation amount of binding (Bmax) was 278±24 fmol/mg protein. Also, the dissociation constant ($K_D$) of [$^3$H]mepyramine was $3.30±0.26×10^{-9}$ M, and the slope as analyzed in accordance with Hill plots was 1.005.

Test Example 3

$LTD_4$ Receptor binding inhibitory test:

10 mM piperadine N,N'-bis(2-ethane sulfonate) buffer (pH 7.5, 0.3 ml) containing 0.2 nM [$^3$H] leukotriene $D_4$, guinea pig lung protein, and a test compound was incubated at 22° C. for 30 minutes. Reaction was stopped by addition of ice-cold Tris-HCl/NaCl (10 mM/100 mM, pH 7.5) buffer, and immediately thereafter, the reaction mixture was filtered by use of a Wattman CF/C filter. The filter was washed twice, each time with 20 ml ice-cold buffer. Radioactivity of the residue was measured by use of a liquid scintillation counter. In a manner similar to that applied to the case of the $H_1$ receptor, $IC_{50}$ and the dissociation constant ($K_D$) of the test compound were obtained (see Table 4). In a saturation test, 2 μM leukotriene $D_4$ was used for the measurement of the amount of non-specific binding.

From the saturation test, it was found that there was involved a single type of receptor, and the saturation amount of binding (Bmax) was 988 fmol/mg protein. Also, the dissociation constant ($K_D$) of [$^3$H]leukotriene $D_4$ was $2.616×10^{-10}$ M, and the slope as analyzed in accordance with Hill plots was 0.99.

TABLE 4

| Example | $H_1$ Receptor $K_D$(M) | $LTD_4$ Receptor $K_D$(M) |
|---|---|---|
| 3 | $4.31 \times 10^{-12}$ | $5.50 \times 10^{-5}$ |
| 4 | $1.64 \times 10^{-7}$ | $1.27 \times 10^{-5}$ |
| 5 | $4.69 \times 10^{-11}$ | $5.44 \times 10^{-5}$ |
| 10 | $3.51 \times 10^{-11}$ | $9.86 \times 10^{-6}$ |
| 11 | $5.95 \times 10^{-12}$ | $2.00 \times 10^{-5}$ |
| 12 | $2.38 \times 10^{-11}$ | $1.58 \times 10^{-5}$ |
| 13 | $1.15 \times 10^{-9}$ | $1.90 \times 10^{-5}$ |
| 14 | $3.96 \times 10^{-12}$ | $9.89 \times 10^{-5}$ |
| 15 | $3.10 \times 10^{-9}$ | $8.06 \times 10^{-6}$ |

Example 4

Test on migration into the brain:

The test was performed in accordance with a method described by Zang. M Q et al. [J. Med. Chem., 38, 2472–2477, 1995]. Briefly, several mice each weighing 20–23 g were provided, and to each mouse was intraperitoneally administered a test sample having a predetermined concentration. One hour later, each mouse was sacrificed and its brain was removed. The brain tissue was mixed with 30 mM Na, K phosphate buffer (pH 7.5) so as to attain a concentration of 40 ml/g wet weight, and the mixture was homogenized. The homogenate was dispensed into three test tubes (900 μl), and a [³H]mepyramine solution (100 μl, final concentration 0.5 nM) was added. The mixture was incubated at 37° C. for 50 minutes. Subsequently, reaction was stopped by addition of ice-cold phosphate buffer, and immediately thereafter, the reaction mixture was filtered by use of a Wattman CF/C filter. The filter was washed twice, each time with 20 ml ice-cold buffer. Radioactivity of the residue was measured by use of a liquid scintillation counter. From the value as obtained when a test compound was not added and values as obtained when the test compound was added at different concentrations, there was determined a dose-response curve representing suppression action of the test compound, from which a 50% inhibitory concentration ($IC_{50}$) was obtained. The cerebral migration index, BPindex, was calculated from the following equation. The results are shown in Table 5.

BPindex=$IC_{50}$ (mg/kg)/dissociation constant for $H_1$ recepters (nM)

TABLE 5

| Compound | $IC_{50}$(mg/kg · ex vivo) | BP index |
|---|---|---|
| Example 10 | 33 | 930 |
| Terfenadine | 26 | 0.17 |

As described above, the piperidine derivative or a salt thereof according to the present invention is endowed with anti-histaminic activity and antileukotriene activity, minimally migrates into the brain, and exhibits lesser side effects such as drowsiness.

What is claimed is:

1. A piperidine derivative represented by the following formula (1) or a salt thereof:

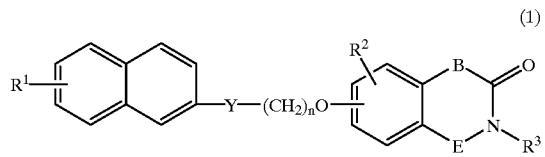

(1)

wherein $R^1$ represents a hydrogen atom or a halogen atom; $R^2$ represents a hydrogen atom or a lower alkyl group; Y represents

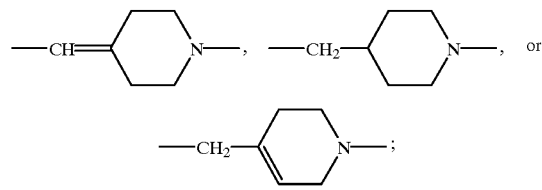

represents a single bond,

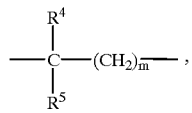

—S—$CH_2$—, or —CH=CH—, wherein each of $R^4$ and $R^5$, which are identical to or different from each other, represents a hydrogen atom or a lower alkyl group, and m represents a number between 0 and 2 inclusive; n represents a number between 2 and 5 inclusive; Z is an oxygen atom and $R^3$ is a hydrogen atom, or $R^3$ and Z may join with the adjacent nitrogen atom to form a tetrazolyl group; and E represents a single bond or a trimethylene group; provided that when B is a single bond, E is a trimethylene group, and when B is a group other than a single bond, E is a single bond.

2. A pharmaceutical composition comprising a piperidine derivative as described in claim 1 or a salt thereof, and a pharmacologically acceptable carrier.

3. A method for the treatment of an allergic disease, which method comprises administering to a patient in need thereof an effective amount of a piperidine derivative as described in claim 1 or a salt thereof.

4. A method for the treatment of a disease selected from the group consisting of asthma, allergic rhinitis, allergic conjunctivitis, atopic dermatitis, urticaria, psoriasis, rheumatism, inflammatory colitis, cerebral ischemia, and cerebral apoplexy, which method comprises administering to a patient in need thereof an effective amount of a piperidine derivative as described in claim 1 or a salt thereof.

* * * * *

UNITED STATES PATENT AND TRADEMARK OFFICE
CERTIFICATE OF CORRECTION

PATENT NO. : 6,107,308
DATED : August 22, 2000
INVENTOR(S) : Hendrick Timmerman et al.

Page 1 of 2

It is certified that error appears in the above-identified patent and that said Letters Patent is hereby corrected as shown below:

Title page,
Item [57], ABSTRACT, first drawing,

"
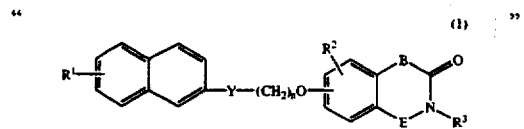
"

should read

--
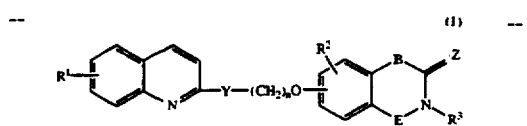
--

Column 2,
Line 52,

"
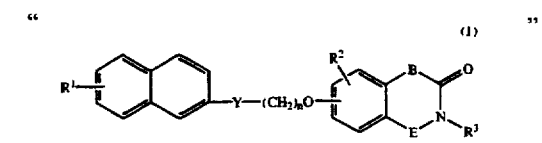
"

should read

--
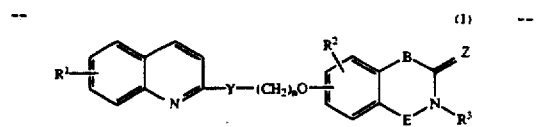
--

UNITED STATES PATENT AND TRADEMARK OFFICE
CERTIFICATE OF CORRECTION

PATENT NO.   : 6,107,308
DATED        : August 22, 2000
INVENTOR(S)  : Hendrick Timmerman et al.

It is certified that error appears in the above-identified patent and that said Letters Patent is hereby corrected as shown below:

Column 15, claim 1,
Line 36,

"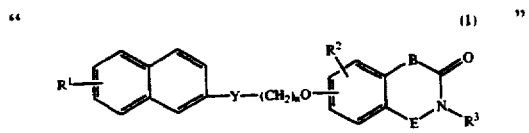 (I) "

should read

-- 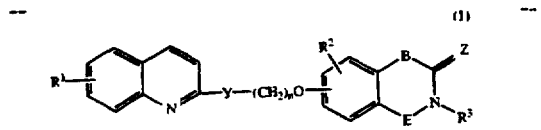 (I) --

Column 16, claim 1,
Line 11, "represents a single bond," should read -- B represents a single bond, --

Signed and Sealed this

Eighteenth Day of December, 2001

Attest:

JAMES E. ROGAN
*Attesting Officer*     *Director of the United States Patent and Trademark Office*